(12) United States Patent
Paskavitz (10) Patent No.: US 9,808,175 B1
(45) Date of Patent: Nov. 7, 2017

(54) METHOD AND SYSTEM FOR ANALYZING IMAGES TO QUANTIFY BRAIN ATROPHY

(75) Inventor: James F. Paskavitz, Holden, MA (US)

(73) Assignee: PAREXEL International Corporation, Waltham, MA (US)

( * ) Notice: Subject to any disclaimer, the term of this patent is extended or adjusted under 35 U.S.C. 154(b) by 626 days.

(21) Appl. No.: 12/698,786

(22) Filed: Feb. 2, 2010

Related U.S. Application Data (60) Provisional application No. 61/149,303, filed on Feb. 2, 2009.

(51) Int. Cl.
*A61B 5/055* (2006.01)

(52) U.S. Cl.
CPC .................................. *A61B 5/055* (2013.01)

(58) Field of Classification Search
CPC ................. G06F 19/321; G06T 7/0012; G06T 2207/30004; A61B 5/055
USPC ................................................. 382/128–132
See application file for complete search history.

(56) References Cited

U.S. PATENT DOCUMENTS

| | | | |
|---|---|---|---|
| 8,150,497 B2* | 4/2012 | Gielen et al. ................. | 600/427 |
| 2005/0010097 A1* | 1/2005 | Cline ............................ | 600/407 |
| 2006/0182321 A1* | 8/2006 | Hu et al. ...................... | 382/128 |
| 2006/0239519 A1* | 10/2006 | Nowinski et al. ............ | 382/128 |
| 2008/0123923 A1* | 5/2008 | Gielen et al. ................. | 382/131 |
| 2009/0171184 A1* | 7/2009 | Jenkins et al. ............... | 600/411 |
| 2009/0292198 A1* | 11/2009 | Kleiven et al. ............... | 600/416 |

OTHER PUBLICATIONS

Cahn et al., "Brain Volume Changes in First-Episode Schizophrenia", Arch Gen Psychiatry, p. 1002-1010, vol. 59, Nov. 2002.*
Nestor, Sean M., "Ventricular Enlargement as a Possible Measure of Alzheimer's Disease Progression Validated Using the Alzheimers' Disease Neuroimaging Initiative Database", *Brain* vol. 131, pp. 2443-2454, 2008.

\* cited by examiner

*Primary Examiner* — Jonathan K Ng
(74) *Attorney, Agent, or Firm* — Wolf, Greenfield & Sacks, P.C.

(57) ABSTRACT

A technique for reliably measuring brain atrophy based on image data, such as data collected as part of an MRI scan of a subject's brain. Rather than measure anatomical features of the brain in one of the scan planes as output by an MRI system, the image data is reformatted to generate a slice that may be transverse to those scan planes. The transverse slice is generated by determining a location of anatomical landmarks and reformatting the image data to represent a slice through these anatomical landmarks. The Anterior and Posterior Commissures are useful landmarks and ventricle area is a useful characteristic to measure from the slice. The rate of change of this measured characteristic can be tracked to determine disease progression and may be useful for diagnosis or evaluation of treatments, and the technique may be applied during clinical trials.

20 Claims, 5 Drawing Sheets

METHOD AND SYSTEM FOR ANALYZING IMAGES TO QUANTIFY BRAIN ATROPHY

RELATED APPLICATIONS

This Application claims priority under 35 U.S.C. §119(e) to U.S. Provisional Application Ser. No. 61/149,303, entitled "METHOD AND SYSTEM FOR ANALYZING IMAGES TO QUANTIFY BRAIN ATROPHY" filed on Feb. 2, 2009, which is herein incorporated by reference in its entirety.

BACKGROUND OF INVENTION

The progression of some disease conditions may be ascertained by structural changes in anatomical structures. For example, expansion of brain ventricles in patients with Alzheimer's disease (AD) occurs as a consequence of brain tissue loss with disease progression. Measuring ventricular size over time is useful for monitoring disease progression and may be used, for example, to assess the therapeutic effects of drugs or other treatments that prevent or slow disease progression.

It is known that ventricular size can be measured using Magnetic Resonance Imaging (MRI) techniques, including automated voxel-based morphometric (VBM) approaches, manual or semi-automated volumetric segmentation algorithms, and linear measurements. However, these methods can be affected by image quality, take a long time, and/or be difficult to reproduce.

Figure 6:
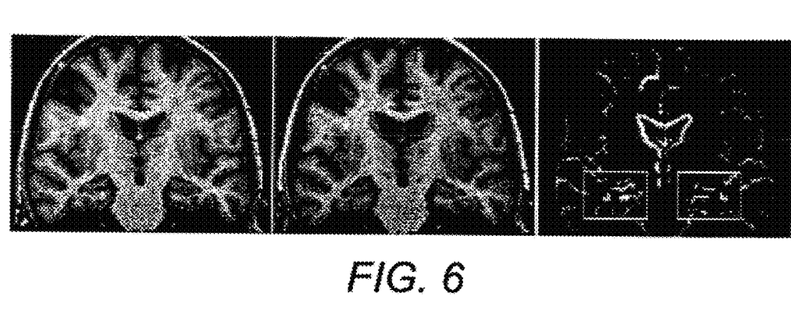
FIG. 6 is a series of images illustrating a technique for measuring changes in volume of a cerebral structure.

A technique for measuring changes in volume of cerebral structures, which could be used for measuring changes in ventricular size, is described in: The boundary shift integral: an accurate and robust measure of cerebral volume changes from registered repeat MRI; Freeborough, P. A.; Fox, N. C.; IEEE Transactions on Medical Imaging, Volume 16, Issue 5, October 1997 Page(s):623-629 (which is hereby incorporated by reference in its entirety). An example of images used in this process are illustrated in FIG. 6.

Another technique, called Brain Parenchymal Fraction (BPF) was also described in Rudick R A, Fisher E, Lee J C, et al. Brain atrophy in relapsing multiple sclerosis: relationship to relapses, EDSS, and treatment with interferon beta-1a. Mult Scler2000; 6:365-372 (which is hereby incorporated by reference in its entirety).

SUMMARY

In one aspect, the invention may be embodied as a method of image analysis. The method involves formatting information from a three dimensional image of an anatomical region based on the location of landmarks identified in that three dimensional image. The information may be formatted as an image of a slice in a position selected based on at least the position of the first anatomical landmark and the position of the second anatomical landmark. A characteristic of an anatomical feature within the image of the slice may be measured. Changes in the measured characteristic may be tracked over time and used as a measure of rate of brain atrophy or progression of a disease or syndrome. All or portions of the method may be performed by processing within a processor.

Accordingly, the invention may relate to a method of analyzing image data comprising a 3-dimensional representation of a brain. The method may include, with at least one processor, obtaining an indication of a position of a first anatomical landmark in the 3-dimensional representation and an indication of a position of a second anatomical landmark in the 3-dimensional representation. The method may also include formatting the image data as a slice through the first anatomical landmark and the second anatomical landmark and measuring a characteristic of an anatomical feature in the slice.

The invention may also relate to a method of performing a clinical trial involving a plurality of subjects, each subject being assigned to a group of a plurality of groups. The method may include, for each of the plurality of subjects, processing image data comprising a plurality of 3-dimensional representation of a brain of the subject by, for each of the plurality of 3-dimensional representations, with at least one processor, generating a slice through a first anatomical landmark and a second anatomical landmark from the 3-dimensional representation. The method may also include measuring a characteristic of an anatomical feature in the slice; and storing the measured characteristic in at least one computer-storage medium. An indicator of an average change of the measured characteristic for each of the plurality of groups may be computed from the stored characteristics.

In another aspect, the invention may be embodied as a system for image analysis. The system may include an imaging unit and one or more components that control or process data from the imaging unit. The system may include computer storage media having computer-executable instructions, that, when executed, perform a method of image analysis.

One or more of the inventive concepts described herein may be embodied as a tool, plug-in or auxiliary component for a clinical trial data collection system.

Accordingly, the invention may relate to at least one non-transitory computer-readable medium, comprising computer-executable instructions, when executed by a processor, for analyzing image data comprising a 3-dimensional representation of a brain by obtaining an indication of a position of a first anatomical landmark in the 3-dimensional representation and an indication of a position of a second anatomical landmark in the 3-dimensional representation. The computer-executable instructions may generate a slice through the first anatomical landmark and the second anatomical landmark from the image data and measure a characteristic of an anatomical feature in the slice.

The foregoing is a non-limiting summary of the invention, which is defined by the appended claims.

BRIEF DESCRIPTION OF DRAWINGS

The accompanying drawings are not intended to be drawn to scale. In the drawings, each identical or nearly identical component that is illustrated in various figures is represented by a like numeral. For purposes of clarity, not every component may be labeled in every drawing. In the drawings.

DETAILED DESCRIPTION OF INVENTION

The inventors have developed a method of analyzing images to measure characteristics of anatomical features, such as brain ventricles, that is more resistant to image quality issues, is quicker, and more accurately reflects atrophy over a short period of time than other imaging methods.

The method is applied in connection with a volumetric or three dimensional image of the brain. Imaging techniques are known for generating three dimensional images of anatomical structures, including the brain. One example of a three dimensional imaging technique is Computed Tomography (CT). CT images may be formed by measuring the attenuation of X-ray radiation as it passes through a region of a subject's anatomy. A CT system collects such attention data for X-rays passing through the region from multiple directions. Sufficient data is collected that a computer can, through a series of complex calculations, "reconstruct" the anatomy that must exist in order to give rise to the attenuation actually measured by the CT system. The reconstructed anatomy can then be displayed pictorially as a human perceptible image or otherwise processed.

In a CT system, the region of anatomy which is irradiated is usually relatively thin, sometimes called a "slice." To reconstruct a three dimensional object, the CT system is operated to scan a larger region of a patient. During a scan, attenuation measurements are taken for adjacent slices over a period of time. The machine collects these measurements in a way that the spatial position of the slices is preserved. Once anatomical information is computed for multiple slices, the anatomical information in separate slices can be correlated, allowing the computer to create a three dimensional representation of the entire anatomical region covered by the scan.

This three dimensional information can be formatted by the computer for display or further processing in any suitable way. For example, the computer may select a portion of the three dimensional information that represents a plane through the subject that is transverse to the planes through which the X-rays passed while the CT system collected X-ray attenuation data during the scan.

As another example of an imaging technique, Magnetic Resonance Imaging (MRI) images may be formed by controlling Radio Frequency (RF) and magnetic fields in a region of the anatomy and measuring the resulting energy that emanates from that region. As with CT imaging, a computer in an MRI system can compute from the measured data information about the anatomy that must have given rise to the measurements. This anatomical information can be collected over a three-dimensional volume and formatted for analysis.

In an example embodiment described herein, MRI imaging is used to collect anatomical information. However, the method of analyzing images as described herein may be employed on CT images or images formed using any other technique that generates suitable images of the anatomical structure to be analyzed.

Regardless of the manner in which images are acquired, they may be analyzed to extract information. In accordance with some embodiments, images of the brain are analyzed according to a method that determines a characteristic of an anatomical structure. This information is derived in an accurate and repeatable fashion, making the method of analyzing images well suited for use in clinical trials in which charges over time in anatomical structures are to be studied.

Figure 1:
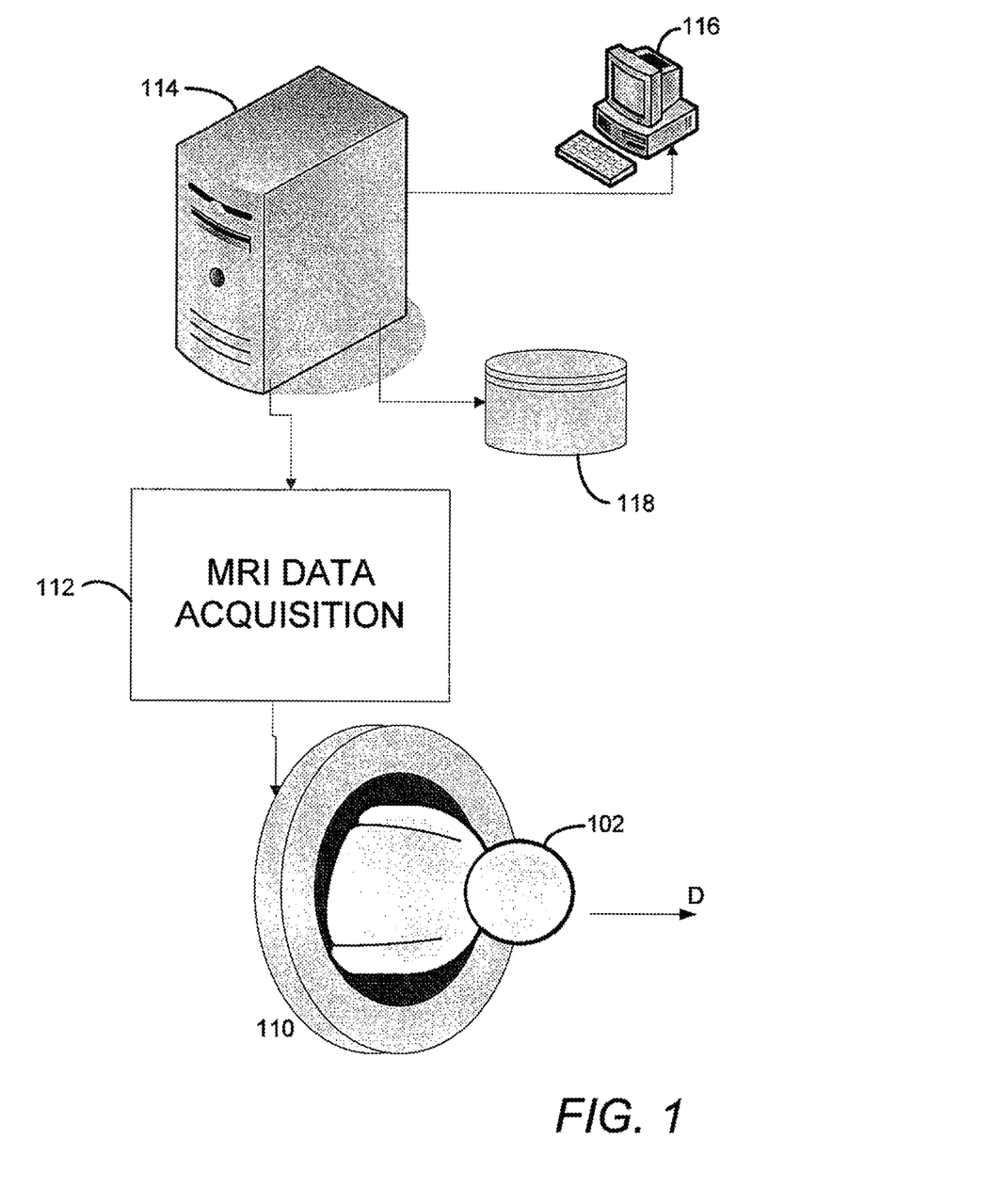
FIG. 1 is a schematic illustration of an exemplary embodiment of a system for quantifying brain atrophy.

The methods described herein may be performed using anatomical information obtained using commercially available systems for acquiring and formatting three dimensional anatomical images. FIG. 1 illustrates an environment in which embodiments of the invention may be practiced.

FIG. 1 illustrates a subject 102 for which a ventricular volume is to be measured. Subject 102 may be a patient participating in a clinical trial to determine the effectiveness of a drug in treating Alzheimer's Disease or other pathological condition in which brain atrophy is a symptom or effect.

As shown, subject 102 is positioned in an imaging unit 110 of a medical imaging system. In the embodiment illustrated, the medical imaging system is a high resolution MRI system, such as an MPRAGE/SPGR MRI system as is known in the art, and imaging unit 110 may be an imaging unit as is known in the art. Such a unit may generate and measure radiation indicative of regions of the anatomy of subject 102. Though, any suitable medical imaging unit may be used.

The medical imaging system includes a data acquisition unit 112 that controls and acquires data from imaging unit 110. Data acquisition unit 112 may be a data acquisition unit as is known in the art. Such a unit may contain circuitry and one or more computer processors programmed to control imaging unit 110 to collect data representative of a portion of the anatomy of subject 102. Though, any suitable data acquisition unit may be employed.

In the scenario illustrated, data acquisition unit 112 controls imaging unit 110 to collect data representative of the anatomy within the brain of subject 102. This data is provided to analysis unit 114. Analysis unit 114 may be an analysis unit as is known in the art. Such a unit may contain one or more computer processors and/or other circuitry to convert data acquired by data acquisition unit 112 into information representing anatomy of the brain of subject 102. The conversion may be performed using software programmed to perform data processing according to known techniques, but any suitable approach for deriving information concerning the anatomy of the brain of subject 102 may be used.

The specific information provided by analysis unit 114 may be controlled by a control program and/or user input. In the embodiment illustrated, computer 116 is networked to analysis unit 114 and provides a user interface through which a user may provide input controlling analysis unit 114 to provide images of specific portions of the anatomy of subject 102. In the embodiment illustrated, user input or a program executing on computer 116 provides control inputs to analysis unit 114 to obtain an image representing a slice through the brain of subject 102 containing multiple landmarks.

As a specific example, a slice containing both the Anterior and Posterior Commissures (AC and PC, respectively) of the brain of subject 102 may be obtained from analysis unit 114. The inventor has recognized that a slice containing the AC and PC is useful for comparison of brain anatomy in images acquired at different times. As a result, performing an analysis on a slice selected to contain these features is useful in circumstances where disease progression is studied.

Though, any suitable landmarks may be used to select the portion of the information for analysis.

The AC and PC may be identified in any suitable way. For example, brain images are formatted in the axial plane. An image reviewer/analyst may manually locate the slice where the AC and the PC are seen on the same axial image and create a ventricular measurement (length, width, area, volume) using semi-automated tools that retain the measurement on the image.

Figure 4A:
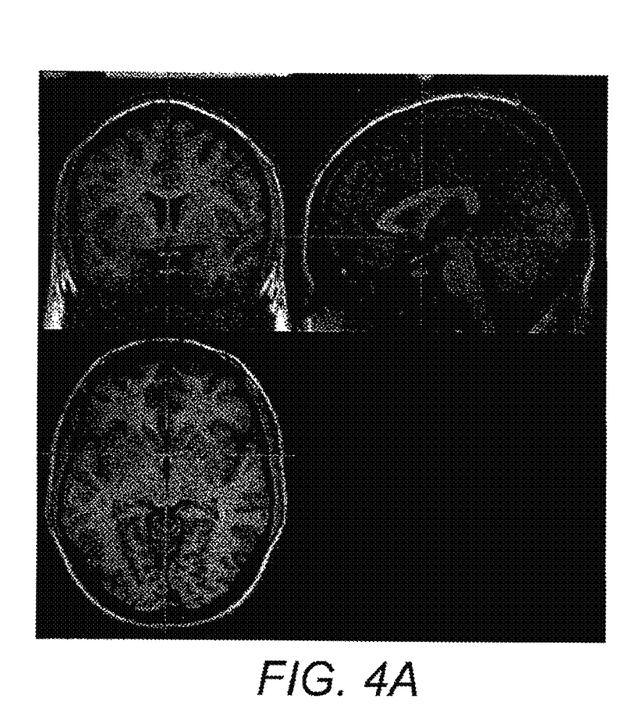
FIG. 4A is MRI image data depicting three slices through a brain, including the Anterior Commissure.

FIG. 4A illustrates images of three slices through a brain. Each of these images shows, at the center of the "crosshairs," the AC. Techniques for locating the AC are known in the art and any suitable technique may be applied. The AC location may be identified in these images by automated image recognition techniques executed by a computer, such as computer 116. Alternatively, the location of the AC may be specified by a user, such as a user interacting with the imaging system through a user interface provided by computer 116. For example, the user could activate a mouse or other pointing device to identify the AC in an image presented on a graphical user interface of computer 116. As a further alternative, the location of the AC may be determined in a semi-automated fashion. A user could, for example, identify an approximate location of the AC in an image of a slice displayed in a graphical user interface of computer 116 and computer analysis of that image could more accurately identify the location.

Regardless of whether examination is performed by a human user or computer image processing, one or more images of various slices through the brain may be examined until a slice is identified in which the AC is visible. Once the location of the AC is determined, that location may be provided to analysis unit 114 as one of the points defining a slice for further analysis. The location may be provided in a coordinate system used by analysis unit 114. For example, in the example of FIG. 4A, the AC is located in X,Y,Z coordinates of (91, 131, 67). An X,Y,Z coordinate system is used in this example because some known imaging machines output image data in such a coordinate system. Though, it should be appreciated that this example is to illustrate that an indication of a position of an anatomical landmark can be obtained, but that the representation of that position is not critical to the invention.

Figure 4B:
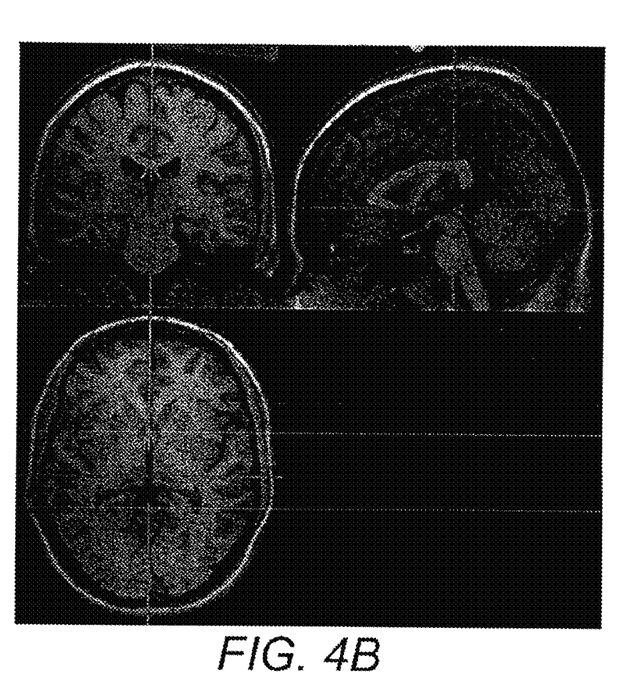
FIG. 4B is MRI image data depicting three slices through a brain, including the Posterior Commissure.

The PC may be identified in a similar way. FIG. 4B illustrates images of slices through the same brain illustrated in FIG. 4A. However, these slices show the PC in the "cross hairs." Here, the PC is located at coordinates (91, 103, 70). Once the locations of the AC and PC are found, image data representing a plane containing these two points may be generated by analysis unit 114. Here, a slice in a plane perpendicular to the scan direction, D (FIG. 1), through these two points may be selected for further analysis.

As noted above, imaging systems that can generate three dimensional information can format this information for display and/or further processing. Generating an image representative of a slice, regardless of the orientation of that slice, is one way in which such information may be formatted. Input provided from computer 116 may identify the landmark locations and/or the slice orientation. Though, image information may be selected based on any suitable criteria that may be specified in any suitable way.

Regardless of the manner in which information for further analysis is specified or formatted, computer 116 may perform or assist a user perform analysis functions on that information. In the embodiment illustrated, the analysis functions involve measuring a characteristic of an anatomical feature in the slice selected to contain identified landmarks.

In the embodiment illustrated in FIG. 1, the anatomical feature is the third ventricle and the characteristic measured is the area of the third ventricle. The area of the third ventricle may be measured in any suitable way, including through automated processing, manual image processing or partially automated processing. In the embodiment illustrated, semi-automated processing is used. A human user identifies the approximate boundaries of the third ventricle as it appears in the selected slice. Computerized image analysis is then used to identify the boundaries of the structure and compute the area within the boundaries. These operations may be performed with image processing techniques as known in the art. Though, any suitable approach for determining the area of the anatomical feature may be employed.

The area of the anatomical feature provides a data point representing brain atrophy in subject 102 at one point in time. That data point may be stored, such as in a database 118, for later use. Database 118 may be a commercially available database, such as an Oracle database. Though, information may be recorded in any suitable fashion.

In an embodiment in which the system of FIG. 1 is used as part of a clinical trial, information recorded in database 118 will identify the subject 102 to which that data point relates. Other data points will be stored for other subjects who are part of the clinical trial. In addition, for each data point, information may be stored to identify when that data point was collected. That data point may also be correlated to study-related information, such as the treatment group to which the subject 102 belongs, the facility at which the data point was collected, the actual images used to compute the data point or other information that may be useful in conducting the clinical trial.

If the system of FIG. 1 is used to determine brain atrophy of an individual patient, such as when brain atrophy is measured as part of treatment of a patient, the data point may still be stored. In this scenario, rather than storing the data point in conjunction with information about a clinical trial, it may be stored along with information relevant to the treatment of the patient.

FIG. 1 illustrates components of a system that may be used to collect data points providing information from which brain atrophy may be determined. The components may be in the same location, such as within a hospital or a clinic. Though, there is no requirement that all or any of the components of the system be in the same location or used at the same time. For example, imaging unit 110 and analysis unit 114 may be in different locations, and connected over a computer network. Likewise, computer 116 may be in a different location from some or all of the other components illustrated in FIG. 1.

Further, it should be appreciated that an imaging system may have more or fewer components than illustrated in FIG. 1. For example, functions of data acquisition unit 112 and analysis unit 114 may be preferred in the same computer hardware. Similarly, functions of computer 116 may be performed in analysis unit 114 or vice versa. Moreover, though only one user computer 116 is shown, multiple user computers may be present to allow multiple users to access study data. Thus, FIG. 1 should be understood to be only an example of components that may be present in same embodiments. Also, it is not necessary that the data points be collected in real time as a scan is performed on a subject. Either the data acquired in the scan and or the information derived from that data by analysis unit 114 may be stored and processed at a later time. Accordingly, the acts within the method of acquiring a data point illustrated in FIG. 2 may be performed at any suitable times in any suitable locations.

Figure 2:
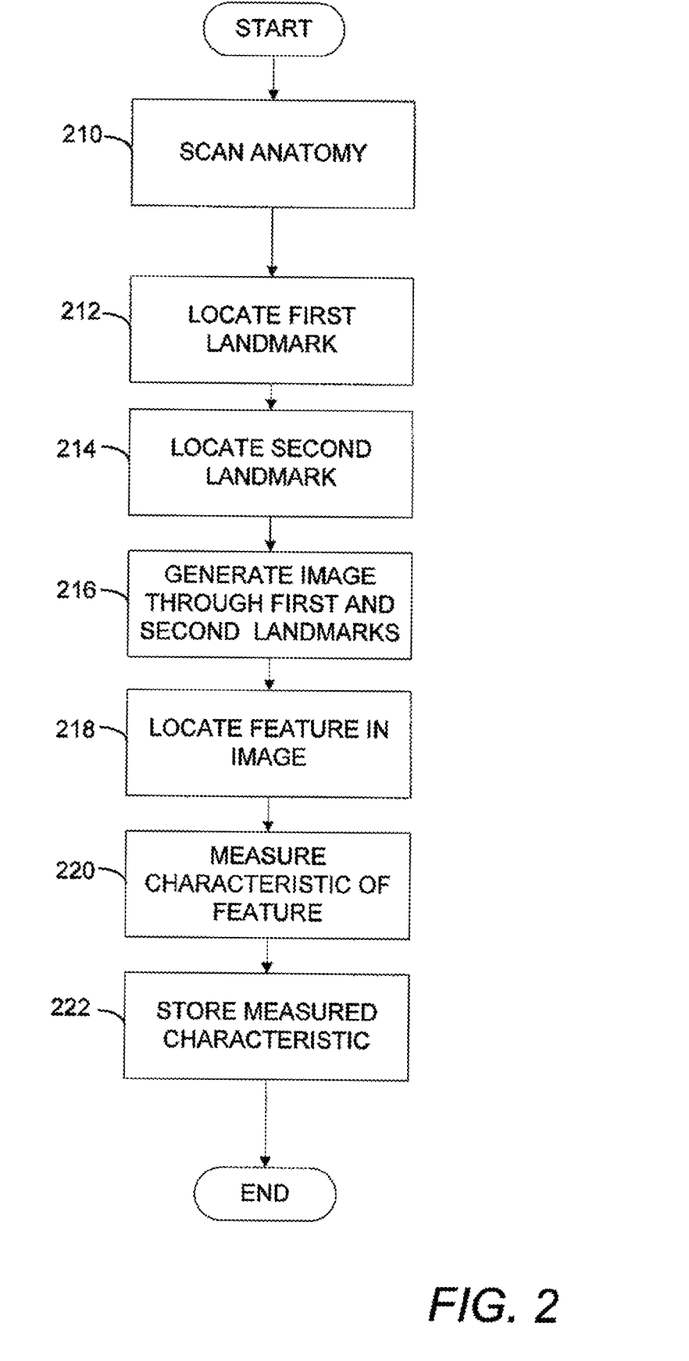
FIG. 2 is a flowchart of an exemplary embodiment of a method of recording data for quantifying brain atrophy.

Turning to FIG. 2, the method begins at block 210 where information on the anatomy of the subject is obtained. This step may involve, for example, an MRI scan of the subject's brain, which generates a 3-dimensional representation of the subject's brain. That 3-dimensional representation may be a series of parallel planes, each representing a slice through a portion of the brain. This image data, can be reformatted, such as by computer processing to generate a slice from any orientation. That slice may be transverse to the scan the parallel planes in which the MRI data was acquired. In blocks 212, 214 and 216, processing to generate such a slice may be performed.

At block 212 and 214, anatomical landmarks are located based on the scan data. As noted above, these landmarks may be the AC and PC. Though, for other embodiments, other landmarks may be used.

At block 216, an image of a slice through the landmarks is generated.

At block 218, an anatomical feature is located in this image. As noted above, this feature may be the third ventricle. Though, for other embodiments, other features may be used.

At block 220, a characteristic of the identified feature is measured. This measurement may be made based on calculations on the image generated at block 216. For example, the area of the third ventricle may be computed from the image, which has been found to be a significant and useful measure of brain atrophy. Though, for other embodiments, other characteristics may be measured including length, width, volume or circumference of one or more identified features.

At block 222, the measurement may be stored as a data point for a subject in the study.

The processing illustrated in FIG. 2 may be performed by one or more machines, such as those illustrated in FIG. 1. Though, processing at some of the blocks illustrated in FIG. 2 may be performed wholly or partially by a human user of the system, such as a clinician engaged to read MRI images of study subjects.

The processing of FIG. 2 may be repeated for the same subject from time to time such that changes in the anatomical feature may be tracked. The processing may also be repeated for multiple subjects in multiple groups such that statistically significant comparisons between groups can be made. For example, one group may represent a study control and another group may receive a drug being investigated in the study. Though, more than two groups could be formed, with subjects in different non-control groups receiving differing amounts of the investigational drug.

Regardless of the number of subjects or the number of groups involved in the study, once the study data is collected, it may be analyzed to determine changes in the anatomical feature. Such changes may be determined based on changes in the measured characteristic of that feature.

Figure 3:
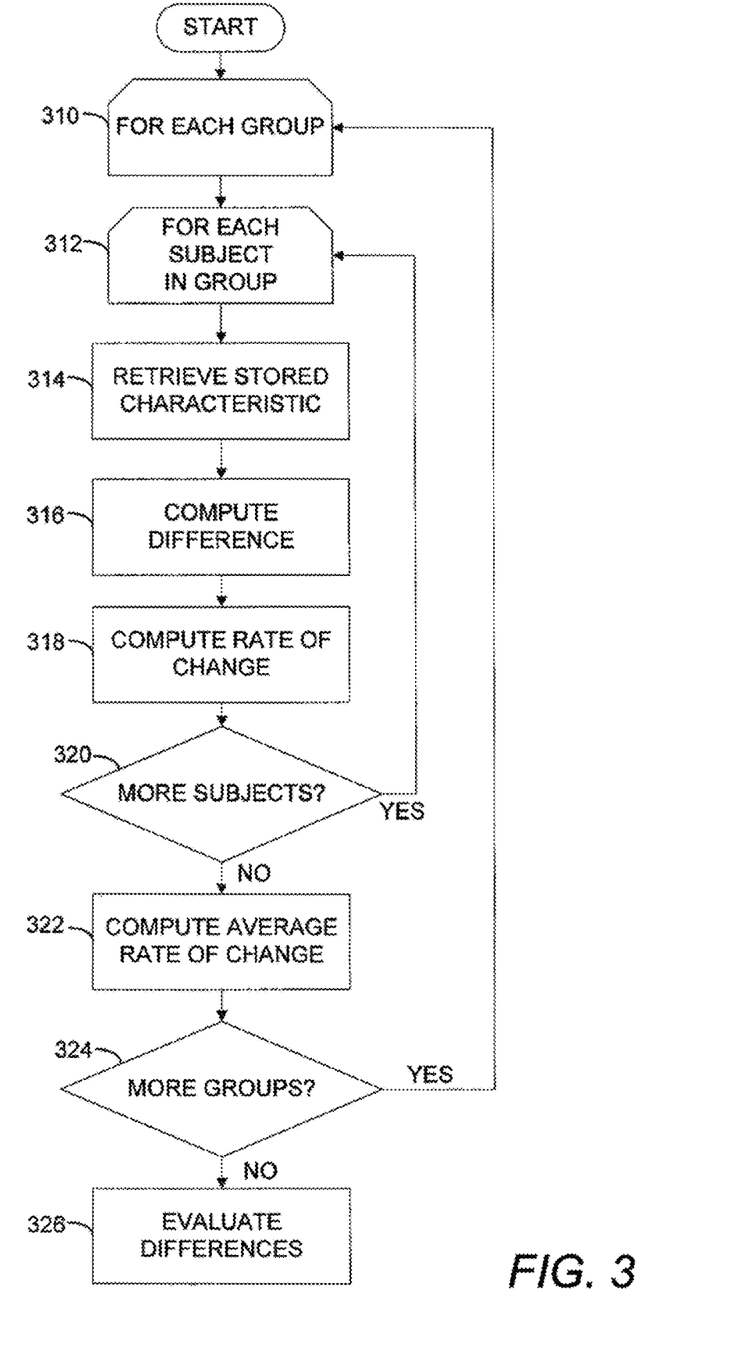
FIG. 3 is a flowchart of an exemplary embodiment of a method of performing a clinical trial in which brain atrophy is a measured variable.

FIG. 3 illustrates processing that may be performed on study data collected for multiple subjects in multiple groups according to the method of FIG. 2. The processing of FIG. 3 may be performed in or controlled from a computer programmed to perform the method illustrated. Though, the method may be implemented in any suitable way.

Turning to FIG. 3, the embodiment illustrated starts at loop start 310. Loop start 310 represents the start of a processing loop that is performed for each group in the study.

The process proceeds to loop start 312. Loop start 312 represents the start of a processing loop that is performed for each subject in a group. As noted above in connection with FIG. 1, information stored in database 118—or other suitable location—may identify a study group with which each subject is associated. This information may be used to identify the groups and the subjects within each group.

Regardless of the manner by which a subject within a group is identified, at block 314, stored information is retrieved for that subject. The stored information may include the measured characteristics stored for the subject, such as the characteristics stored at block 222 (FIG. 2). In the embodiment illustrated in which the study involves comparing the rate of brain atrophy between study groups, ventricle area measured for each subject at a plurality of instances in time may be retrieved at block 314 for processing.

Figure 5A:
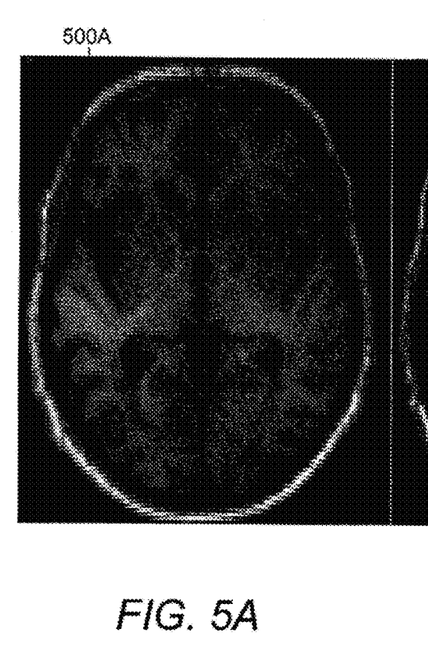
FIG. 5A is a slice through the Anterior Commissure and the Posterior Commissure of the brain of a subject generated from a 3-dimensional representation of a brain of a subject obtained from MRI image data showing the third ventricle.
Figure 5B:
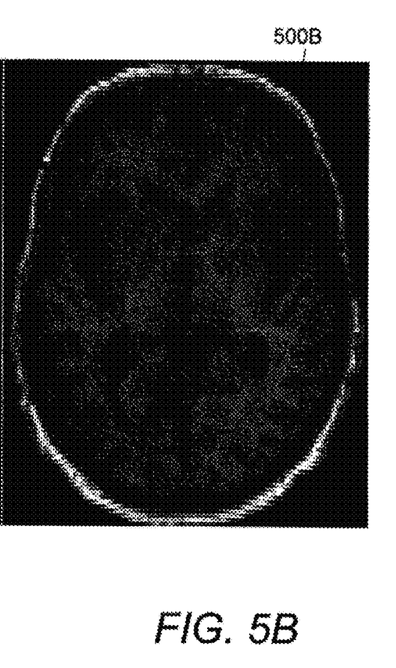
FIG. 5B is a slice through the brain of the same subject illustrated in FIG. 5A, formed at a later time from which changes in the third ventricle can be determined.

At block 316, that processing includes determining the change between successive measurements of the characteristic. FIGS. 5A and 5B illustrate such a comparison graphically. FIG. 5A illustrates an image of a slice selected as described above. The third ventricle has been outlined with outline 510A by a computer processing that image. The area enclosed by outline 510A represents a characteristic of the anatomical feature. FIG. 5B represents an image of a slice selected in the same way for the same subject at a later instant in time. The area enclosed by outline 510B represents a characteristic of the anatomical feature at a later instant in time. The difference between these areas represents the change. According to some embodiments, changes of a few percent in area may be reliably detected.

At block 318, that difference may be converted to a rate of change by normalizing by the time between successive measurements of the characteristic. The time interval between successive measurements may be based on the study parameters. In a study, it may be desirable to obtain data as quickly as possible, suggesting a short time between successive measurements. However, the time interval between measurements should be long enough that a difference in the characteristic being measured will be detected.

Accordingly, the time interval may depend partially on the rate of change being measured. In addition, the measurement technique also dictates the time between the successive measurements. If a measurement interval is so short that the change in the measured characteristic over that interval is small relative to errors associated with the measurement technique, measurements of change will be unreliable. The technique described above that includes measuring an area of the third ventricle in a slice containing the AC and the PC results in repeatable measurements. Errors introduced through measurement differences from one data point to the next that can occur with some prior art techniques are reduced. Consequently, the interval between successive data points can be relatively short. As an example, the measurement interval may be on the order of a few months. In some embodiments, the measurement interval is about 6 months.

Regardless of the interval between measurements for a subject, once the rate of change of the characteristic for that subject is determined the process may loop back from decision block 320 to loop start 312 when there are more subjects in a group for which data remains to be processed. Data for each subject in the group is then processed in a similar fashion.

Once data points for all of the subjects in a group is processed, the process of FIG. 3 branches from decision block 320 to block 322. At block 322, an average rate of change of all subjects in the group is computed.

The processing then proceeds to decision block 324. From decision block 324, the process loops back to loop start 310 if there are more groups for which data remains to be processed. The next group is selected and processing for that group is performed as above.

Processing for each group is performed. When an average value is computed for each group, the process branches from decision block 324 to block 326. At block 326, an evaluation is made of the differences between groups. The specific evaluation may depend on the nature of the study being conducted. For example, when evaluating the effectiveness of a drug, the evaluation at block 326 may include determining whether any difference in the rate of change between one or more study groups and a control group is statistically significant. Though, an suitable evaluation may be performed, depending on the nature of the study being conducted.

EXAMPLE

We used the unprocessed SPGR/MPRAGE MRI scans from the ADNI database of 110 Normal Control (C) and 105 AD subjects who had a baseline and 6 month follow-up scan for image analysis and compared them for longitudinal changes. Image analysts were blinded to time point and diagnosis. The two time point images were reformatted simultaneously to assure comparable slice location/angle from the sagittal to the axial plane with the Anterior and Posterior Commissures (AC and PC, respectively) required to be identified in the same slice. Using an edge detection tool in our image analysis software suite (Alice), analysts segmented the third ventricle for both time points in this axial slice with the AC and PC as the boundaries. The 3rd ventricle area was automatically calculated by the Alice software. Though, one of skill in the art will recognize that other known software tools may be used for this calculation. Difference scores for the area measurements over the 6 month scans were statistically tested using baseline scores as the covariate in ANCOVA.

Mean 3rd Ventricle area in the plane of the AC and PC was 159 mm2 at baseline and 163 mm2 at 6 months with a non-significant 3.2% change for Cs. AD subjects were 185 mm2 at baseline and 195 mm2 at 6 months with a significant 6.4% change (ANCOVA, p=0.0133).

The inventor believes this data to demonstrate that processing as described herein provides a quick and simple approach to image analysis of hi-resolution MRI scans for AD progression and probably monitoring treatment effects in clinical trials. The 6.4% change in 3rd Ventricle area noted at 6 months for the AD group is comparable to other analysis approaches, such as the VBM ventricular boundary shift integral and semi-automated lateral ventricle volume segmentation. The potential advantages of a method as described herein is that it is insensitive to image artifacts, does not require unblinding the time point or morphing/coregistering the images (unlike VBM) and is faster than VBM and lateral ventricle volume segmentation. Also the 3rd Ventricle area in the axial AC-PC plane is easy to identify.

Having thus described several aspects of at least one embodiment of this invention, it is to be appreciated that various alterations, modifications, and improvements will readily occur to those skilled in the art.

For example, though the present invention is illustrated in conjunction with a process of tacking the progression of Alzheimer's Disease, there are many diseases where ventricle size are relevant. These diseases include multiple sclerosis, Huntington's, fronto-temporal dementia, Lewy body dementia all exhibit atrophy over time (ventricles increase in size). Other syndromes where ventricles are big and then shrink with treatment are Normal Pressure Hydrocephalus/Communicating Hydrocephalus and Obstructive Hydrocephalus. The techniques described herein may be used in conjunction with the diagnosis or study of any or all of these diseases or syndromes or other diseases for which atrophy is a characteristic.

Further, it was described that comparisons of ventricle sizes may be used to determine a rate of change of the ventricle. It should be appreciated that size measurements as described herein may be used to identify other changes, including changes in the rate of change, or even used to determine size, per se. Such other metrics may be employed, for example, in studies in which multiple measurements are taken and the rate of change is non-linear over the measurement interval. Though, any suitable metric may be computed based on the requirements of a study or patient treatment needs.

As a further example, it was described that two points, representing positions of anatomical landmarks, were used to orient a slice to be generated from three dimensional image data. Any number of points may be obtained. For example, three points could be obtained from three features detectable in the image data. In this case, a plane may be selected that passed through the position of a first anatomical landmark and the position of a second anatomical landmark in addition to through the position of a third anatomical landmark. If more than three points are obtained, other approaches may be used to select the position of the slice, such as by making a best fit among the positions of the landmarks. Also, it should be noted that the slice may be positioned relative to the landmarks, which need not necessarily include passing through the landmarks. For example, the slice could be positioned at a fixed offset from the landmarks Such alterations, modifications, and improvements are intended to be part of this disclosure, and are intended to be within the spirit and scope of the invention. Accordingly, the foregoing description and drawings are by way of example only.

The above-described embodiments of the present invention can be implemented in any of numerous ways. For example, steps of the processing described herein may be implemented using hardware, software or a combination thereof. When implemented in software, the software code can be executed on any suitable processor or collection of processors, whether provided in a single computer or distributed among multiple computers.

Further, it should be appreciated that a computer may be embodied in any of a number of forms, such as a rack-mounted computer, a desktop computer, a laptop computer, or a tablet computer. Additionally, a computer may be embedded in a device not generally regarded as a computer but with suitable processing capabilities, including a Personal Digital Assistant (PDA), a smart phone or any other suitable portable or fixed electronic device.

Also, a computer may have one or more input and output devices. These devices can be used, among other things, to present a user interface. Examples of output devices that can be used to provide a user interface include printers or display screens for visual presentation of output and speakers or other sound generating devices for audible presentation of output. Examples of input devices that can be used for a user interface include keyboards, and pointing devices, such as mice, touch pads, and digitizing tablets. As another example, a computer may receive input information through speech recognition or in other audible format.

Such computers may be interconnected by one or more networks in any suitable form, including as a local area network or a wide area network, such as an enterprise network or the Internet. Such networks may be based on any suitable technology and may operate according to any suitable protocol and may include wireless networks, wired networks or fiber optic networks.

Also, the various methods or processes outlined herein may be coded as software that is executable on one or more processors that employ any one of a variety of operating systems or platforms. Additionally, such software may be written using any of a number of suitable programming languages and/or programming or scripting tools, and also may be compiled as executable machine language code or intermediate code that is executed on a framework or virtual machine.

In this respect, the invention may be embodied as a computer readable medium (or multiple computer readable media) (e.g., a computer memory, one or more floppy discs, compact discs, optical discs, magnetic tapes, flash memories, circuit configurations in Field Programmable Gate Arrays or other semiconductor devices, or other tangible, non-transitory computer storage medium) encoded with one or more programs that, when executed on one or more computers or other processors, perform methods that implement the various embodiments of the invention discussed above. The computer readable medium or media can be transportable, such that the program or programs stored thereon can be loaded onto one or more different computers or other processors to implement various aspects of the present invention as discussed above.

The terms "program" or "software" are used herein in a generic sense to refer to any type of computer code or set of computer-executable instructions that can be employed to program a computer or other processor to implement various aspects of the present invention as discussed above. Additionally, it should be appreciated that according to one aspect of this embodiment, one or more computer programs that when executed perform methods of the present invention need not reside on a single computer or processor, but may be distributed in a modular fashion amongst a number of different computers or processors to implement various aspects of the present invention.

Computer-executable instructions may be in many forms, such as program modules, executed by one or more computers or other devices. Generally, program modules include routines, programs, objects, components, data structures, etc. that perform particular tasks or implement particular abstract data types. Typically the functionality of the program modules may be combined or distributed as desired in various embodiments.

Also, data structures may be stored in computer-readable media in any suitable form. For simplicity of illustration, data structures may be shown to have fields that are related through location in the data structure. Such relationships may likewise be achieved by assigning storage for the fields with locations in a computer-readable medium that conveys relationship between the fields. However, any suitable mechanism may be used to establish a relationship between information in fields of a data structure, including through the use of pointers, tags or other mechanisms that establish relationship between data elements.

Various aspects of the present invention may be used alone, in combination, or in a variety of arrangements not specifically discussed in the embodiments described in the foregoing and is therefore not limited in its application to the details and arrangement of components set forth in the foregoing description or illustrated in the drawings. For example, aspects described in one embodiment may be combined in any manner with aspects described in other embodiments.

Also, the invention may be embodied as a method, of which an example has been provided. The acts performed as part of the method may be ordered in any suitable way. Accordingly, embodiments may be constructed in which acts are performed in an order different than illustrated, which may include performing some acts simultaneously, even though shown as sequential acts in illustrative embodiments.

Also, the phraseology and terminology used herein is for the purpose of description and should not be regarded as limiting. The use of "including," "comprising," or "having," "containing," "involving," and variations thereof herein, is meant to encompass the items listed thereafter and equivalents thereof as well as additional items.

What is claimed is:

1. A method of analyzing image data comprising a 3-dimensional representation of a brain collected with an imaging device, the method comprising:

with at least one processor:

obtaining an indication of a position of a first anatomical landmark in a 3-dimensional representation of a brain collected during a first imaging session and an indication of a position of a second anatomical landmark in the 3-dimensional representation of the brain collected during the first imaging session; and computing, from the 3-dimensional representation of the brain collected during the first imaging session, a first slice with an orientation in the 3-dimensions, wherein the orientation of the first slice is selected based on the obtained position of the first anatomical landmark and the obtained position of the second anatomical landmark such that the orientation of the first slice is not constrained by an orientation of the imaging device and the first slice encompasses:

a position selected based on at least the position of the first anatomical landmark and a position selected based on at least the position of the second anatomical landmark;

obtaining an indication of a position of the first anatomical landmark in a 3-dimensional representation of a brain collected during a second imaging session and an indication of a position of a second anatomical landmark in the 3-dimensional representation of the brain collected during the second imaging session;

computing, from the 3-dimensional representation of the brain collected during the second imaging session, a second slice with an orientation in the 3-dimensions, wherein the orientation of the second slice is selected based on the obtained position of the first anatomical landmark and the obtained position of the second anatomical landmark such that the orientation of the second slice is not constrained by an orientation of the imaging device, wherein the orientation of the second slice with respect to the orientation of the imaging device is different than the orientation of the first slice with respect to the orientation of the imaging device, and wherein the second slice encompasses:

a position selected based on at least the position of the first anatomical landmark and a position selected based on at least the position of the second anatomical landmark; and measuring a change in a characteristic of an anatomical feature based on a comparison of information from the first slice to information from the second slice to track the change in the characteristic of the anatomical feature over time.

2. The method of claim 1, wherein obtaining an indication of a position of a first anatomical landmark and an indication of a position of a second anatomical landmark comprises receiving user input.

3. The method of claim 1, wherein obtaining an indication of the position of the first anatomical landmark and an indication of the position of the second anatomical landmark comprises performing an automated analysis of the 3-dimensional representation.

4. The method of claim 1, wherein the first anatomical landmark is an Anterior Commissure and the second anatomical landmark is a Posterior Commissure.

5. The method of claim 1, wherein the anatomical feature is a third ventricle.

6. The method of claim 1, wherein the measured characteristic of the anatomical feature is an area of the anatomical feature.

7. The method of claim 1, wherein the measured characteristic of the anatomical feature comprises one or more of length, width, volume or circumference of the anatomical feature.

8. The method of claim 1, wherein measuring a characteristic of the anatomical feature comprises:
with the at least one processor:
receiving user input identifying an approximate boundary of the anatomical feature in the first slice;
determining boundaries of the anatomical feature; and
computing an area within the determined boundaries.

9. The method of claim 1, wherein
measuring a change in the characteristic of the anatomical feature comprises
measuring, based on the information from the first slice, the characteristic of the anatomical feature;
storing the measured characteristic of the anatomical feature from the first slice as a first measured characteristic;
measuring, based on the information from the second slice, the characteristic of the anatomical feature; and
measuring a change in the characteristic of the anatomical feature as a difference between the measured characteristic from the second slice and the first measured characteristic.

10. The method of claim 1, wherein:
the method further comprises acquiring the image data during each of the first and second imaging sessions by performing a magnetic resonance imaging (MRI) scan on the brain of a subject, the image data comprising a plurality of parallel slices providing the 3-dimensional representation of the brain; and
wherein the orientation of each of the first slice and the second slice is transverse to the plurality of parallel slices.

11. A method of performing a clinical trial involving a plurality of subjects, each subject being assigned to a group of a plurality of groups, the method comprising:

for each of the plurality of subjects, processing a first 3-dimensional representation of a brain of the subject collected with an imaging device during a first imaging session and second 3-dimensional representation of the brain collected with the imaging device during a second image session, wherein processing the first 3-dimensional representation comprises:
with at least one processor:
obtaining an indication of a position of a first anatomical landmark in the first 3-dimensional representation of a brain and an indication of a position of a second anatomical landmark in the first 3-dimensional representation of the brain;
generating a first slice through the first anatomical landmark and the second anatomical landmark from the first 3-dimensional representation, wherein the first slice has an orientation in the 3-dimensions, and wherein the orientation of the first slice is selected based on the obtained position of the first anatomical landmark and the obtained position of the second anatomical landmark such that the orientation of the first slice is not constrained by an orientation of the imaging device and the first slice encompasses:
a position selected based on at least the position of the first anatomical landmark and
a position selected based on at least the position of the second anatomical landmark;
measuring a characteristic of an anatomical feature in the first slice; and
storing the measured characteristic as a first measured characteristic in at least one computer-storage medium;
wherein processing the second 3-dimensional representation comprises:
with the at least one processor:
obtaining an indication of a position of the first anatomical landmark in the second 3-dimensional representation of a brain and an indication of a position of a second anatomical landmark in the second 3-dimensional representation of the brain;
generating a second slice through the first anatomical landmark and the second anatomical landmark from the second 3-dimensional representation, wherein the second slice has an orientation in the 3-dimensions, and wherein the orientation of the second slice is selected based on the obtained position of the first anatomical landmark and the obtained position of the second anatomical landmark such that the orientation of the second slice is not constrained by an orientation of the imaging device, wherein the orientation of the second slice with respect to the orientation of the imaging device is different than the orientation of the first slice with respect to the orientation of the imaging device, and wherein the second slice encompasses:
a position selected based on at least the position of the first anatomical landmark and
a position selected based on at least the position of the second anatomical landmark;
measuring the characteristic of the anatomical feature in the second slice; and
storing the measured characteristic as a second measured characteristic in the at least one computer-storage medium; and
computing from the stored first and second measured characteristics an indicator of an average change of the characteristic for each of the plurality of groups.

12. The method of claim 11, wherein the indicator comprises an average rate of change.

13. The method of claim 12, further comprising, with the at least one processor, determining whether differences in the average rate of change between groups are statistically significant.

14. The method of claim 11, wherein:
each of the first and second 3-dimensional representation of the brain comprises a magnetic resonance imaging (MRI) image of the brain;
the first anatomical landmark is an Anterior Commissure and the second anatomical landmark is a Posterior Commissure;
the anatomical feature is a third ventricle; and
the measured characteristic of the anatomical feature is one or more of area, length, width, volume or circumference of the anatomical feature.

15. At least one non-transitory computer-readable medium,
comprising computer-executable instructions that, when executed by a processor, analyze image data collected with an imaging device by:
obtaining an indication of a position of a first anatomical landmark in a 3-dimensional representation of a brain collected during a first imaging session and an indication of a position of a second anatomical landmark in the 3-dimensional representation of the brain collected during the first imaging session; and
computing, from the 3-dimensional representation of the brain collected during the first imaging session, a first slice with an orientation in the 3-dimensions, wherein the orientation of the first slice is selected based on the obtained position of the first anatomical landmark and the obtained position of the second anatomical landmark such that the orientation of the first slice is not constrained by an orientation of the imaging device and the first slice encompasses:
a position selected based on at least the position of the first anatomical landmark and
a position selected based on at least the position of the second anatomical landmark;
obtaining an indication of a position of the first anatomical landmark in a 3-dimensional representation of a brain collected during a second imaging session and an indication of a position of the second anatomical landmark in the 3-dimensional representation of the brain collected during the second imaging session; and
computing, from the 3-dimensional representation of the brain collected during the second imaging session, a second slice with an orientation in the 3-dimensions, wherein the orientation of the second slice is selected based on the obtained position of the first anatomical landmark and the obtained position of the second anatomical landmark in the second 3-dimensional representation such that the orientation of the second slice is not constrained by an orientation of the imaging device, wherein the orientation of the second slice with respect to the orientation of the imaging device is different than the orientation of the first slice with respect to the orientation of the imaging device, and wherein the second slice encompasses:
a position selected based on at least the position of the first anatomical landmark and
a position selected based on at least the position of the second anatomical landmark; and
measuring a change in a characteristic of mi anatomical feature based on a comparison of information from the first slice to information from the second slice to track the change in the characteristic of the anatomical feature over time.

16. The at least one non-transitory computer-readable medium of claim 15, wherein:
the computer-executable instructions for obtaining the indication of the position of the first anatomical landmark and the indication of the position of the second anatomical landmark comprises computer-executable instructions for analyzing the 3 dimensional representation of the brain to determine the position of the first anatomical landmark and the indication of the position of the second anatomical landmark.

17. The at least one non-transitory computer-readable medium of claim 15, wherein:
the first anatomical landmark is an Anterior Commissure and the second anatomical landmark is a Posterior Commissure.

18. The at least one non-transitory computer-readable medium of claim 17, wherein the anatomical feature is a ventricle.

19. The at least one non-transitory computer-readable medium of claim 18, wherein:
the computer-executable instructions for measuring the change of the characteristic of the anatomical feature comprise computer-executable instructions for:
receiving user input identifying an approximate boundary of the anatomical feature in each of the first and second slices;
determining boundaries of the anatomical feature in each of the first and second slices; and
computing an area within the determined boundaries in each of the first and second slices.

20. The at least one non-transitory computer-readable medium of claim 19, further comprising computer-executable instructions for storing the computed area in association with information relating to a clinical trial.

* * * * *

UNITED STATES PATENT AND TRADEMARK OFFICE
CERTIFICATE OF CORRECTION

PATENT NO. : 9,808,175 B1
APPLICATION NO. : 12/698786
DATED : November 7, 2017
INVENTOR(S) : James F. Paskavitz It is certified that error appears in the above-identified patent and that said Letters Patent is hereby corrected as shown below:

In the Claims

Claim 15, Column 16, Line 12:
measuring a change in a characteristic of mi anatomical
Should read:
measuring a change in a characteristic of an anatomical Signed and Sealed this
Sixth Day of March, 2018

Andrei Iancu
*Director of the United States Patent and Trademark Office*